(12) United States Patent
Wang et al.

(10) Patent No.: US 12,388,064 B2
(45) Date of Patent: Aug. 12, 2025

(54) OPTICAL SENSOR PACKAGE STRUCTURE AND ELECTRONIC DEVICE

(71) Applicant: QINGDAO GOERTEK INTELLIGENT SENSOR CO., LTD, Qingdao (CN)

(72) Inventors: Kui Wang, Qingdao (CN); Dexin Wang, Qingdao (CN); Yanmei Sun, Qingdao (CN); Haiqiang Song, Qingdao (CN)

(73) Assignee: QINGDAO GOERTEK INTELLIGENT SENSOR CO., LTD, Qingdao (CN)

( * ) Notice: Subject to any disclaimer, the term of this patent is extended or adjusted under 35 U.S.C. 154(b) by 457 days.

(21) Appl. No.: 17/999,954

(22) PCT Filed: Dec. 10, 2020

(86) PCT No.: PCT/CN2020/135395
§ 371 (c)(1),
(2) Date: Nov. 28, 2022

(87) PCT Pub. No.: WO2021/238150
PCT Pub. Date: Dec. 2, 2021

(65) Prior Publication Data
US 2023/0246012 A1    Aug. 3, 2023

(30) Foreign Application Priority Data
May 29, 2020    (CN) .......................... 202010472882.7

(51) Int. Cl.
*H01L 25/16* (2023.01)
*H01L 23/00* (2006.01)
(Continued)

(52) U.S. Cl.
CPC ............ *H01L 25/167* (2013.01); *H01L 24/16* (2013.01); *A61B 5/1455* (2013.01);
(Continued)

(58) Field of Classification Search
CPC ... H01L 25/167; H01L 24/16; H01L 23/3121; A61B 5/1455
See application file for complete search history.

(56) References Cited

U.S. PATENT DOCUMENTS 9,018,661 B2 *    4/2015    Pindl .................. H10H 20/8506
                                                    257/98
9,590,129 B2 *    3/2017    Deliwala ............... H10F 55/255
(Continued)

FOREIGN PATENT DOCUMENTS

CN    102136457 A    7/2011
CN    104893310 A    9/2015
(Continued)

OTHER PUBLICATIONS

First Office Action issued in Chinese Patent Application No. 202010472882.7; mailed Aug. 3, 2021; 13 pgs.
(Continued)

*Primary Examiner* — Laura M Menz
(74) *Attorney, Agent, or Firm* — HAUPTMAN HAM, LLP (57) ABSTRACT

Disclosed are an optical sensor package structure and a device. The optical sensor package structure includes a substrate, a signal processing chip, a photodiode and a potting adhesive layer. The signal processing chip provided on a surface of the substrate is provided with a conductive through hole, and the signal processing chip is electrically connected to the substrate via the conductive through hole. The photodiode provided on a surface of the signal processing chip away from the substrate is electrically connected to
(Continued)

the substrate via the conductive through hole. The potting adhesive layer is for wrapping the signal processing chip and the photodiode, and an elongation at break of the potting adhesive layer is greater than 40%.

13 Claims, 3 Drawing Sheets

(51) Int. Cl.
    *A61B 5/1455*     (2006.01)
    *H01L 23/31*     (2006.01)
    *H01L 23/48*     (2006.01)

(52) U.S. Cl.
    CPC ........ *H01L 23/3121* (2013.01); *H01L 23/481* (2013.01); *H01L 24/17* (2013.01); *H01L 2224/16145* (2013.01); *H01L 2224/16227* (2013.01); *H01L 2224/17181* (2013.01); *H01L 2924/12043* (2013.01)

(56) References Cited

U.S. PATENT DOCUMENTS

| | | | | |
|---|---|---|---|---|
| 2013/0161683 | A1* | 6/2013 | Hamamoto | ............ C08L 83/04 524/588 |
| 2014/0014995 | A1* | 1/2014 | Pindl | .................... H10H 20/854 438/27 |
| 2014/0070348 | A1* | 3/2014 | Yee | .................... H10F 39/8053 257/E31.127 |
| 2016/0141440 | A1* | 5/2016 | Chun | .................... H10F 55/255 257/82 |
| 2018/0138127 | A1* | 5/2018 | Lee | ....................... H01L 23/562 |
| 2022/0173151 | A1* | 6/2022 | Xiang | ................... H10F 39/018 |
| 2023/0246012 | A1* | 8/2023 | Wang | ..................... H01L 24/16 257/82 |

FOREIGN PATENT DOCUMENTS

| | | | | |
|---|---|---|---|---|
| CN | 105140253 | A | | 12/2015 |
| CN | 105176484 | A | * | 12/2015 |
| CN | 108641669 | A | * | 10/2018 |
| CN | 108778098 | A | | 11/2018 |
| CN | 109524385 | A | | 3/2019 |
| CN | 109661435 | A | | 4/2019 |
| CN | 110484025 | A | * | 11/2019 ............. C08G 77/38 |
| CN | 110993513 | A | | 4/2020 |
| CN | 111009475 | A | | 4/2020 |
| CN | 111033743 | A | * | 4/2020 ............. H01L 21/56 |
| CN | 111090145 | A | | 5/2020 |
| CN | 111640739 | A | * | 9/2020 ......... A61B 5/02427 |
| CN | 211929487 | U | * | 11/2020 ........ A61B 5/02427 |
| CN | 213633515 | U | * | 7/2021 |
| CN | 111640739 | B | * | 3/2022 ......... A61B 5/02427 |
| CN | 114868006 | A | * | 8/2022 ........ B01L 3/502715 |
| CN | 116830213 | A | * | 9/2023 ............... C01B 3/12 |
| CN | 118620213 | A | * | 9/2024 |
| CN | 119105002 | A | * | 12/2024 ............... G01D 4/02 |
| CN | 119351035 | A | * | 1/2025 |
| CN | 119410324 | A | * | 2/2025 |
| CN | 119431715 | A | * | 2/2025 |
| CN | 119505797 | A | * | 2/2025 |
| CN | 119552629 | A | * | 3/2025 |
| EP | 3041897 | B1 | | 5/2017 |
| EP | 4145508 | A1 | * | 3/2023 ......... A61B 5/02427 |
| EP | 3675178 | B1 | * | 1/2025 ............. G09F 9/301 |
| JP | 2009200534 | A | | 9/2009 |
| WO | WO-2021238150 | A1 | * | 12/2021 ........ A61B 5/02427 |
| WO | WO-2022189947 | A1 | * | 9/2022 ............... C01B 3/12 |
| WO | WO-2024071309 | A1 | | 4/2024 |
| WO | WO-2024173677 | A2 | * | 8/2024 ........... G02B 6/3885 |

OTHER PUBLICATIONS

International Search Report and Written Opinion issued in International Patent Application No. PCT/CN2020/135395; mailed Feb. 25, 2021; 17 pgs.

European Search Report in Corresponding European Application No. 20938289.4, dated Jun. 7, 2024; 11 pgs.

* cited by examiner

OPTICAL SENSOR PACKAGE STRUCTURE AND ELECTRONIC DEVICE

CROSS-REFERENCE TO RELATED APPLICATIONS

This application is the National Stage of International Application No. PCT/CN2020/135395, filed on Dec. 10, 2020, which claims priority to Chinese Patent Application No. 202010472882.7, filed on May 29, 2020, and titled "OPTICAL SENSOR PACKAGE STRUCTURE AND ELECTRONIC DEVICE", the entire disclosure of which is incorporated herein by reference.

TECHNICAL FIELD

The present disclosure relates to the technical field of system in a package, in particular to an optical sensor package structure and an electronic device.

BACKGROUND

Optical sensors (such as heart rate sensors and blood oxygen sensors) are generally provided with photodiodes and light emitting diodes. The light emitted by the light emitting diode is reflected by the capillaries in human tissue, and then the photodiode is irradiated by the light. The heart rate or blood oxygen value of the user can be measured according to a change rule of current component of light current and alternating current. In the related art, the optical sensor package structure is provided with a substrate and a photodiode. Generally, the photodiode is electrically connected to the substrate by wire bonding. When the photodiode is sealed with the potting adhesive, the photodiode and lead wires of the photodiode need to be wrapped completely by the potting adhesive, which will result in a larger thickness of the potting adhesive layer. In this case, the adhesive at the bottom layer will be cured incompletely when the potting adhesive is cured, resulting in poor reliability of the optical sensor package structure.

The above content is only used to assist in understanding the technical solutions of the present disclosure, and does not mean that the above content is the prior art.

SUMMARY

The present disclosure provides an optical sensor package structure and an electronic device, aiming to solve the problem that the adhesive at the bottom layer will be cured incompletely due to a larger thickness of the potting adhesive layer, thereby improving the reliability of the optical sensor package structure.

In order to achieve the above objectives, the present disclosure provides an optical sensor package structure. The optical sensor package structure includes a substrate, a signal processing chip, a photodiode and a potting adhesive layer. The signal processing chip provided on a surface of the substrate is provided with a conductive through hole, and the signal processing chip is electrically connected to the substrate via the conductive through hole. The photodiode provided on a surface of the signal processing chip away from the substrate is electrically connected to the substrate via the conductive through hole. The potting adhesive layer is for wrapping the signal processing chip and the photodiode, and an elongation at break of the potting adhesive layer is greater than 40%.

In an embodiment, a Young's modulus of the potting adhesive layer is lower than 100 MPa.

In an embodiment, a distance between a surface of the potting adhesive layer away from the photodiode and a surface of the photodiode away from the signal processing chip is L, and L is greater than 0 mm and not greater than 0.1 mm.

In an embodiment, a surface of the substrate facing the signal processing chip is provided with a first pad. A surface of the signal processing chip facing the substrate is provided with a redistribution layer. The signal processing chip is electrically connected to the first pad via the conductive through hole and the redistribution layer.

In an embodiment, the surface of the signal processing chip facing the substrate is provided with a solder ball, and the solder ball is electrically connected to the redistribution layer. The first pad is provided with a solder joint, and the solder ball is electrically abutted against the solder joint.

In an embodiment, a photoelectric electrode of the photodiode is configured to face the signal processing chip, and the photoelectric electrode is electrically connected to the substrate via the conductive through hole.

In an embodiment, the photodiode includes two photoelectric electrodes provided on a same side of the photodiode, and when the two photoelectric electrodes are installed, the two photoelectric electrodes are configured to face the signal processing chip and electrically connected to the substrate.

In an embodiment, the optical sensor package structure further includes an outer shell. The outer shell is provided on the surface of the substrate facing the signal processing chip, and a surface of the outer shell away from the substrate is provided with a first installation through groove for exposing the substrate. The signal processing chip and the photodiode are provided in the first installation through groove, and the potting adhesive layer provided in the first installation through groove is for wrapping the signal processing chip and the photodiode.

In an embodiment, the optical sensor package structure further includes a light emitting diode, the light emitting diode is provided on the surface of the substrate facing the signal processing chip and is electrically connected to the substrate. The surface of the outer shell away from the substrate is further provided with a second installation through groove for exposing the substrate, the light emitting diode is provided in the second installation through groove, and the potting adhesive layer is further provided in the second installation through groove and is for wrapping the light emitting diode.

A transmittance of the potting adhesive layer to a light emitted by the light emitting diode is greater than 90%.

The second installation through groove includes an installation groove section and a light guide groove section, the installation groove section and the light guide groove section are sequentially distributed along a direction away from the light emitting diode, and the installation groove section and the light guide groove section are connected with each other, and the light emitting diode is provided in the installation groove section, and an area enclosed by the light guide groove section gradually increases along the direction away from the light emitting diode. The surface of the substrate facing the signal processing chip is provided with a second pad and a third pad, and the light emitting diode is provided with two light emitting electrodes, one of the two light emitting electrodes is electrically connected to the second pad, and the other of the two light emitting electrodes is electrically connected to the third pad.

The light emitting electrode includes a light emitting negative electrode and a light emitting positive electrode, the light emitting negative electrode is electrically connected to the second pad, and the light emitting positive electrode is electrically connected to the third pad.

The optical sensor package structure includes a plurality of the signal processing chips, the plurality of the signal processing chips are provided on the surface of the substrate at intervals, each signal processing chip is provided with a conductive through hole, and each signal processing chip is electrically connected to the substrate via the conductive through hole; the optical sensor package structure includes a plurality of the photodiodes corresponding to the signal processing chips, and one of the photodiodes provided on the surface of the signal processing chip away from the substrate is electrically connected to the substrate via a corresponding conductive through hole; the potting adhesive layer is for wrapping each signal processing chip and a corresponding photodiode.

The present disclosure further provides an electronic device. The electronic device includes the optical sensor package structure. The optical sensor package structure includes a substrate, a signal processing chip, a photodiode and a potting adhesive layer. The signal processing chip provided on a surface of the substrate is provided with a conductive through hole, and the signal processing chip is electrically connected to the substrate via the conductive through hole. The photodiode provided on a surface of the signal processing chip away from the substrate is electrically connected to the substrate via the conductive through hole. The potting adhesive layer is for wrapping the signal processing chip and the photodiode.

In the technical solutions of the present disclosure, the optical sensor package structure includes a substrate, a signal processing chip, a photodiode and a potting adhesive layer. The signal processing chip is provided on a surface of the substrate, the photodiode is provided on a surface of the signal processing chip away from the substrate. The signal processing chip is provided with a conductive through hole for conducting electricity. Both the signal processing chip and the photodiode are electrically connected to the substrate via the conductive through hole. The potting adhesive layer is for wrapping the signal processing chip and the photodiode. In the present disclosure, via the conductive through hole of the signal processing chip, instead of by wire bonding, the photodiode of the optical sensor package structure is electrically connected to the substrate. In this way, the potting adhesive for wrapping the exposed lead wires can be omitted. Therefore, not only the thickness of the potting adhesive layer can be relatively reduced, but also the problem that the potting adhesive at the bottom layer will be cured incompletely due to a larger thickness of the potting adhesive layer can be improved, thereby improving the reliability of the optical sensor package structure. In an embodiment, an elongation at break of the potting adhesive layer is greater than 40%, which can effectively improve the problem of brittle fracture in the potting adhesive layer.

BRIEF DESCRIPTION OF THE DRAWINGS

To illustrate the technical solutions according to the embodiments of the present disclosure or the related art more clearly, the accompanying drawings for describing the embodiments or the related art are introduced briefly in the following. Apparently, the accompanying drawings in the following description are only some drawings in the present disclosure. Persons of ordinary skill in the art can derive other drawings from the accompanying drawings without creative efforts.

The realization of the objective, functional characteristics, and advantages of the present disclosure are further described with reference to the accompanying drawings.

DETAILED DESCRIPTION OF THE EMBODIMENTS

The technical solutions of the embodiments of the present disclosure will be described in detail below with reference to the accompanying drawings. It is obvious that the embodiments described are only some rather than all of the embodiments of the present disclosure. All other embodiments obtained by those skilled in the art based on the embodiments of the present disclosure without creative efforts shall fall within the claimed scope of the present disclosure.

It should be noted that all the directional indications (such as up, down, left, right, front, rear . . . ) in the embodiments of the present disclosure are only used to explain the relative positional relationship, movement, or the like of the components in a certain posture (as shown in the drawings). If the specific posture changes, the directional indication will change accordingly.

Besides, the descriptions associated with, e.g., "first" and "second", in the present disclosure are merely for descriptive purposes, and cannot be understood as indicating or suggesting relative importance or impliedly indicating the number of the indicated technical feature. Therefore, the feature associated with "first" or "second" can expressly or impliedly include at least one such feature. In the description of this disclosure, "plurality" means at least two, such as two, three, etc., unless otherwise clearly and specifically limited.

In the present disclosure, unless otherwise clearly specified and limited, the terms "connected", "fixed", etc. should be interpreted broadly. For example, "fixed" can be a fixed connection, a detachable connection, or a whole; can be a mechanical connection or an electrical connection; may be directly connected, or indirectly connected through an intermediate medium, and may be the internal communication between two elements or the interaction relationship between two elements, unless specifically defined otherwise. For those of ordinary skill in the art, the specific meaning of the above-mentioned terms in the present disclosure can be understood according to specific circumstances.

In addition, the technical solutions of the various embodiments can be combined with each other, but the combinations must be based on the realization of those skilled in the art. When the combination of technical solutions is contradictory or cannot be achieved, it should be considered that such a combination of technical solutions does not exist, nor does it fall within the scope of the present disclosure.

Figure 1:
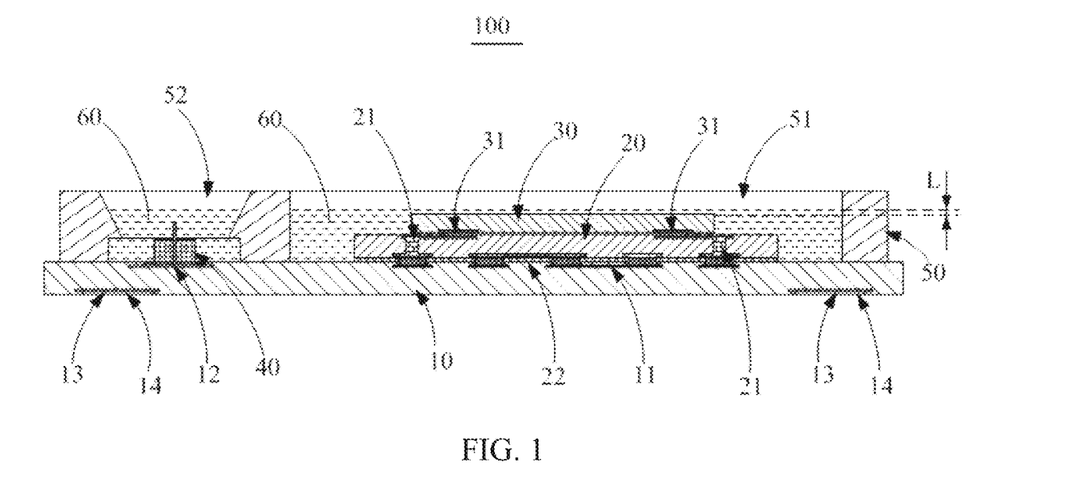
FIG. 1 is a cross-sectional schematic structural diagram of an optical sensor package structure according to an embodiment of the present disclosure.

The present disclosure provides an optical sensor package structure 100, and the optical sensor can be a heart rate sensor, a blood oxygen sensor or other types of optical sensors. As shown in FIG. 1, in an embodiment of the optical sensor package structure 100 of the present disclosure, the optical sensor package structure 100 includes a substrate 10, a signal processing chip 20, a photodiode 30 and a potting adhesive layer 60. The signal processing chip 20 is provided on a surface of the substrate 10, and the signal processing chip 20 is provided with a conductive through hole 21. The signal processing chip 20 is electrically connected to the substrate 10 via the conductive through hole 21. The photodiode 30 is provided on a surface of the signal processing chip 20 away from the substrate 10, and the photodiode 30 is electrically connected to the substrate 10 via the conductive through hole 21. The potting adhesive layer 60 is for wrapping the signal processing chip 20 and the photodiode 30, and an elongation at break of the potting adhesive layer 60 is greater than 40%.

The substrate 10 can be a printed circuit board, which may be a silicon substrate 10, or an epoxy resin substrate 10, etc., A surface of the substrate 10 is provided with a circuit for electrical connection, and the surface of the substrate 10 is further provided with a pad for leading out signals, and the pad for leading out signals is electrically connected to the circuit. Generally, the signal processing chip 20 is an analog front end chip or a microprocessor unit chip (AFE/MPU chip). By a flip chip method, the signal processing chip 20 is attached to the surface of the circuit substrate 10 provided with pads. The flip chip method is an existing patch method, and the specific operations thereof will not be repeated here. The conductive through hole 21 is generally a through silicon hole, and a conductive through silicon hole can be provided at the signal processing chip 20 by through silicon via (TSV). The through silicon hole penetrates both surfaces of the signal processing chip 20, and via the through silicon hole, the signal processing chip 20 is electrically connected to pads on the surface of the substrate 10. Of course, the conductive through hole 21 may also be made of other materials, such as a through tin hole, etc., all of which shall fall within the scope of the present disclosure. By a flip chip method or a die attach method, the photodiode 30 (PD) can be attached to the surface of the signal processing chip 20 away from the substrate 10. Moreover, the photodiode 30 can be electrically connected to the substrate 10 via the conductive through hole 21. Both the flip chip method and the die attach method are existing technologies, and the specific operations thereof will not be repeated here. The potting adhesive is a transparent adhesive for wrapping surfaces of the signal processing chip 20 and the photodiode 30 to position the signal processing chip 20 and the photodiode 30, and a transparent potting adhesive layer 60 is formed after the potting adhesive is cured. Compared to an electrical connection between the photodiode 30 and the substrate 10 by wire bonding, an electrical connection between the photodiode 30 and the substrate 10 via the conductive through hole 21 can omit the potting adhesive for wrapping the exposed lead wires. In this way, the thickness of the potting adhesive layer 60 can be relatively reduced, and the situation that the potting adhesive at the bottom layer will be cured incompletely due to a larger thickness of the potting adhesive layer 60 can be improved, thereby improving the reliability of the optical sensor package structure 100.

When the optical sensor package structure 100 is warping due to a backflow of the potting adhesive, an upper surface of the potting adhesive layer 60 is deformed greatly, which will generate a relatively large normal stress, and a concentrated stress will be generated at the potting adhesive layer 60 near the corners of the photodiode 30. In this case, when a cured adhesive with an elongation at break greater than 40% is used and the thickness of the potting adhesive layer 60 is reduced, the problem of brittle fracture in the potting adhesive layer 60 can be effectively improved.

It should be noted that the electrical connection between the conductive through hole 21 and the substrate 10 is generally realized by connecting wires, or, of course, by using the solder paste. Likewise, the electrical connection between the conductive through hole 21 and the photodiode 30 can be realized by connecting wires, or by using the solder paste.

Therefore, it can be understood that in the technical solution of the present disclosure, the optical sensor package structure 100 includes a substrate 10, a signal processing chip 20, a photodiode 30 and a potting adhesive layer 60. The signal processing chip 20 is provided on the surface of the substrate 10, and the photodiode 30 is provided on a surface of the signal processing chip 20 away from the substrate 10. The signal processing chip 20 is provided with a conductive through hole 21 for conducting electricity, and the photodiode 30 is electrically connected to the substrate 10 via the conductive through hole 21. The potting adhesive layer 60 is for wrapping the signal processing chip 20 and the photodiode 30.

In the present disclosure, via the conductive through hole 21 of the signal processing chip 20, instead of by wire bonding, the photodiode 30 of the optical sensor package structure 100 is electrically connected to the substrate 10. In this way, the potting adhesive for wrapping the exposed lead wires can be omitted. Therefore, not only the thickness of the potting adhesive layer 60 can be relatively reduced, but also the problem that the potting adhesive at the bottom layer will be cured incompletely due to a larger thickness of the potting adhesive layer 60 can be improved, thereby improving the reliability of the optical sensor package structure 100. In an embodiment, an elongation at break of the potting adhesive layer 60 is greater than 40%, which can effectively improve the problem of brittle fracture in the potting adhesive layer 60.

In an embodiment, the potting adhesive layer 60 can be made of at least one of the silicone resin, the epoxy resin and the acrylate.

In an embodiment, a Young's modulus of the potting adhesive layer 60 is lower than 100 MPa.

The potting adhesive is a polymer material with a large thermal expansion coefficient, and a cured adhesive with a Young's modulus lower than 100 MPa is adopted to reduce the thermal stress generated by the optical sensor package structure 100 when the potting adhesive is heated, thereby effectively improving the problem that the package structure is warping greatly when the potting adhesive flows back.

A distance between a surface of the potting adhesive layer 60 away from the photodiode 30 and a surface of the photodiode 30 away from the signal processing chip 20 is L, and L is greater than 0 mm and not greater than 0.1 mm. In this way, the height of the cured potting adhesive layer 60 is reduced and ensured to be lower than 0.1 mm, thereby effectively improving the problem of brittle fracture in the potting adhesive layer 60.

It can be understood that the potting adhesive is a polymer material with a small thermal conductivity. In the present disclosure, the thickness of the potting adhesive layer 60 is relatively small, and the surface height of the potting adhesive layer 60 is relatively low, which not only improves the heat dissipation conditions of the optical sensor package structure 100, but also reduces the temperature gradient of the potting adhesive layer 60 and optimizes the stress of the potting adhesive layer 60.

Figure 2:
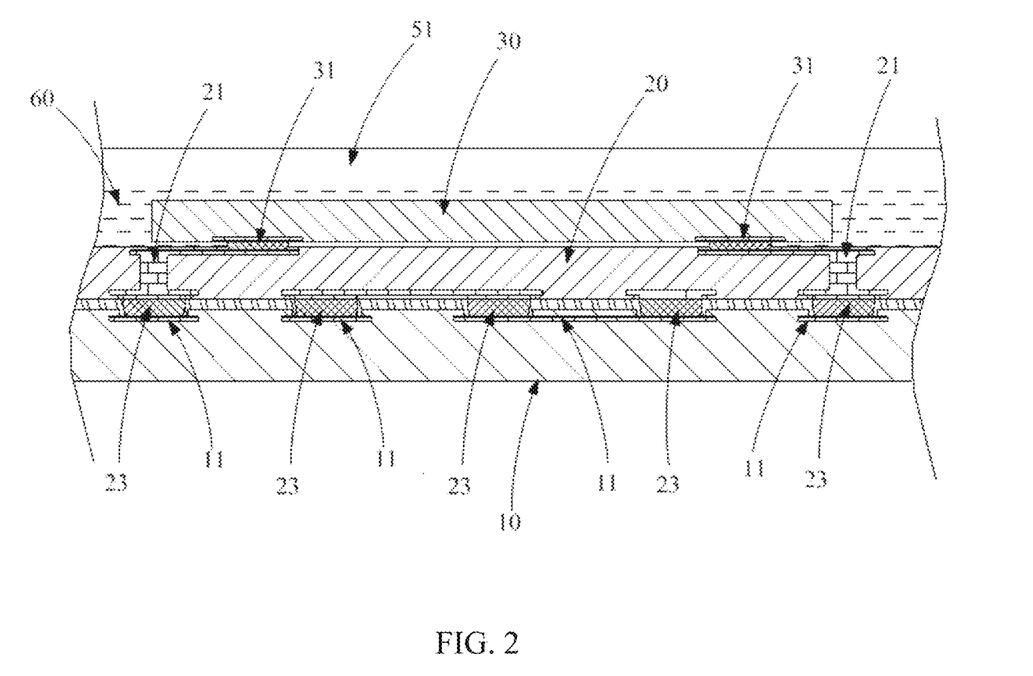
FIG. 2 is a partially enlarged schematic structural diagram of the optical sensor package structure in FIG. 1.

In an embodiment of the present disclosure, a surface of the substrate 10 facing the signal processing chip 20 is provided with a first pad 11, and a surface of the signal processing chip 20 facing the substrate 10 is provided with a redistribution layer 22. The signal processing chip 20 is electrically connected to the first pad 11 via the conductive through hole 21 and the redistribution layer 22.

A redistribution layer 22 (RDL) is provided on a surface of the signal processing chip 20 facing the substrate 10, and the redistribution layer 22 is electrically abutted against the conductive through hole 21 and communicated with the conductive through hole 21. After the signal processing chip 20 is attached to the substrate 10, the signal processing chip 20 is electrically abutted against the first pad 11 and communicated with the first pad 11 on a surface of the substrate 10 via the conductive through hole 21 and the redistribution layer 22. In this way, not only the thickness of the potting adhesive layer 60 can be further reduced in an embodiment, but also the problem that the potting adhesive at the bottom layer will be cured incompletely due to a larger thickness of the potting adhesive layer 60 can be further improved, thereby further improving the reliability of the optical sensor package structure 100.

In an embodiment of the present disclosure, the surface of the signal processing chip 20 facing the substrate 10 is provided with a solder ball 23, and the solder ball 23 is electrically connected to the redistribution layer 22. The first pad 11 is provided with a solder joint, and the solder ball 23 is electrically abutted against the solder joint.

When the signal processing chip 20 is attached to the substrate 10, the solder ball 23 on the surface of the signal processing chip 20 is configured to face the first pad 11 on the surface of the substrate 10. After the signal processing chip 20 is attached to the substrate 10, the solder ball 23 corresponds to the solder joint of the pad (not shown). The solder ball 23 can be electrically connected to the solder joint by soldering the solder ball 23 and the solder joint. By this method, the signal processing chip 20 is electrically connected to the substrate 10, and the method is simple and effective.

In an embodiment, a photoelectric electrode 31 of the photodiode 30 is configured to face the signal processing chip 20, and the photoelectric electrode 31 is electrically connected to the substrate 10 via the conductive through hole 21.

The photodiode 30 includes two photoelectric electrodes 31, namely a photoelectric positive electrode and a photoelectric negative electrode, and the two photoelectric electrodes 31 are provided on a same side of the photodiode 30. When the photodiode 30 is attached to the signal processing chip 20, the two photoelectric electrodes 31 are configured to face the signal processing chip 20. After the photodiode 30 is attached to the signal processing chip 20, the two photoelectric electrodes 31 are electrically connected to the substrate 10 via the conductive through hole 21. The electrical connection between the two photoelectric electrodes 31 and the substrate 10 can be realized by using connecting wires, or by using solder paste. In this way, not only the thickness of the potting adhesive layer 60 can be further reduced in an embodiment, but also the problem that the potting adhesive at the bottom layer will be cured incompletely due to a larger thickness of the potting adhesive layer 60 can be further improved, thereby further improving the reliability of the optical sensor package structure 100.

In an embodiment, as shown in FIG. 1, the optical sensor package structure 100 further includes an outer shell 50. The outer shell 50 is provided on the surface of the substrate 10 facing the signal processing chip 20, and a surface of the outer shell 50 away from the substrate 10 is provided with a first installation through groove 51 for exposing the substrate 10. The signal processing chip 20 and the photodiode 30 are provided in the first installation through groove 51, and the potting adhesive layer 60 provided in the first installation through groove 51 is for wrapping the signal processing chip 20 and the photodiode 30.

The outer shell 50, which can be obtained by injection molding, can be attached to the surface of the substrate 10 facing the signal processing chip 20 by the surface-mount technology (SMT). The outer shell 50 is provided with a first installation through groove 51 for exposing the substrate 10, and the first installation through groove 51 is roughly a square groove. The signal processing chip 20 and the photodiode 30 are provided in the first installation through groove 51. The potting adhesive layer 60 is filled in the first installation through groove 51 for wrapping the signal processing chip 20 and the photodiode 30. It can be understood that the potting adhesive layer 60 is further for wrapping a surface of the substrate 10 in the first installation through groove 51. By providing the outer shell 50, the photodiode 30 and the signal processing chip 20 can be positioned, and the filling operation of the potting adhesive can be facilitated. Of course, the outer shell 50 can be further made of the ceramic, to make the outer shell 50 and the substrate 10 sintered into a whole, all of which shall fall within the scope of the present disclosure.

As shown in FIG. 1, the optical sensor package structure 100 further includes a light emitting diode 40. The light emitting diode 40 is provided on the surface of the substrate 10 facing the signal processing chip 20 and is electrically connected to the substrate 10. The surface of the outer shell 50 away from the substrate 10 is further provided with a second installation through groove 52 for exposing the substrate 10. The light emitting diode 40 is provided in the second installation through groove 52. The potting adhesive layer 60 is further provided in the second installation through groove 52 for wrapping the light emitting diode 40.

The light emitting diode 40 (LED) can be attached to the surface of the substrate 10 facing the signal processing chip 20 by the flip chip method or the die attach method, and the light emitting diode 40 is electrically connected to the substrate 10. Both the flip chip method and the die attach method are existing technologies, and the specific operations thereof will not be repeated here. Corresponding to the light emitting diode 40, the outer shell 50 is provided with a second installation through groove 52 for holding the light emitting diode 40. Similarly, the potting adhesive is further filled in the second installation through groove 52 for wrapping a surface of the light emitting diode 40. Furthermore, the potting adhesive layer 60 is for wrapping a surface of the substrate 10 in the first installation through groove 51, and the potting adhesive layer 60 is obtained after the potting adhesive layer 60 is cured. When the optical sensor package structure 100 is working, a light is emitted by the light emitting diode 40. Then the light passes through the transparent potting adhesive layer 60 and irradiates the capillary in the human tissue. After reflected by the capillary in the human tissue, the light irradiates to the light emitting diode 40. Then a signal reflecting a change rule of current component of light current and alternating current can be transmitted to the signal processing chip 20. By a photoelectric data conversion, the signal is output to reflect heart rate and blood oxygen of the user.

It can be understood that the light emitting diode 40 is provided in the second installation through groove 52, and not only the second installation through groove 52 can position the light emitting diode 40, but also side walls of the second installation through groove 52 can effectively prevent the light of the LED from directly irradiating the photodiode 30, thereby ensuring the measurement accuracy of the optical sensor package structure 100.

In an embodiment, transmittance of the potting adhesive layer 60 to a light emitted by the light emitting diode 40 is greater than 90%. The potting adhesive layer 60 is a transparent adhesive layer, and the transmittance of the transparent adhesive layer to the light emitted by the light emitting diode 40 is greater than 90%, which is beneficial to improve the detection accuracy of the optical sensor package structure 100.

As shown in FIG. 1, the second installation through groove 52 includes an installation groove section 521 and a light guide groove section 522. The installation groove section 521 and the light guide groove section 522 are sequentially distributed along a direction away from the light emitting diode 40, and the installation groove section 521 and the light guide groove section 522 are connected with each other. The light emitting diode 40 is provided in the installation groove section 521, and an area enclosed by the light guide groove section 522 gradually increases along the direction away from the light emitting diode 40.

Figure 3:
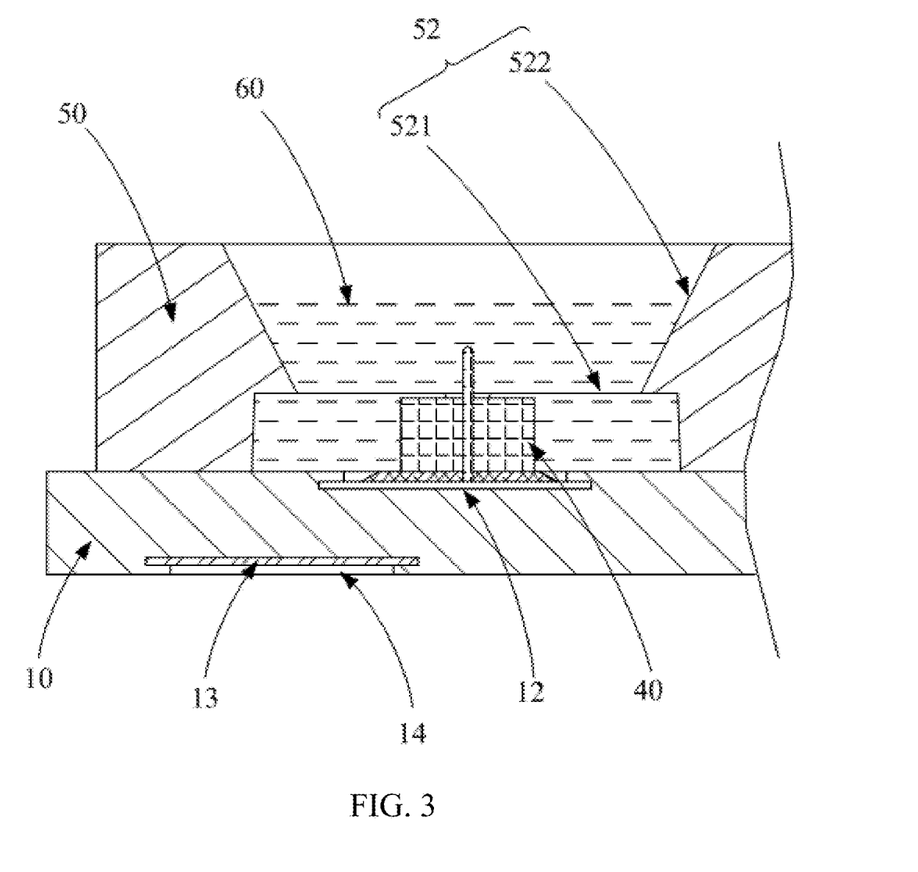
FIG. 3 is another partially enlarged schematic structural diagram of the optical sensor package structure in FIG. 1.

The installation groove section 521 is roughly a square groove for installing the light emitting diode 40, and the light guide groove section 522 is roughly a trapezoidal groove for guiding the light of the light emitting diode 40. The area enclosed by the light guide groove section 522 increases gradually along the direction away from the light emitting diode 40, which not only can effectively focus and emit the light of the light emitting diode 40, but also is beneficial to improve detection accuracy of the optical sensor package structure 100. Of course, the light guide groove section 522 may further be in other shapes, such as a stepped groove shape that the area enclosed by the light guide groove section 522 increases gradually along the direction away from the light emitting diode 40, all of which shall fall within the scope of the present disclosure.

In an embodiment of the present disclosure, the surface of the substrate 10 facing the signal processing chip 20 is provided with a second pad 12 and a third pad (not shown). The light emitting diode 40 is provided with two light emitting electrodes, and one of the two light emitting electrodes is electrically connected to the second pad 12, and the other of the two light emitting electrodes is electrically connected to the third pad.

The light emitting diode 40 is provided with two light emitting electrodes (not shown), namely, a light emitting positive electrode and a light emitting negative electrode. When the light emitting diode 40 is attached to the substrate 10, the light emitting negative electrode of the light emitting diode 40 is configured to face the surface of the substrate 10 provided with the second pad 12, and the light emitting negative electrode is pasted on the second pad 12 by a conductive silver adhesive, to realize the electrical conduction between the light emitting negative electrode and the second pad 12. The light emitting positive electrode of the light emitting diode 40 is electrically connected to the third pad by connecting wires, to realize the electrical conduction between the light emitting diode 40 and the substrate 10.

It should be noted that a conductive layer (not shown) and metal wires (not shown) are provided inside the substrate 10. The first pad 11, the second pad 12, and the third pad on the surface provided of the substrate 10 are electrically connected to each other by the metal wires and the conductive layer.

In addition, the substrate 10 is further provided with an external pad 13. The external pad 13 is electrically connected to the first pad 11, the second pad 12 and the third pad by metal wires and the conductive layer. An exposure opening 14 is provided on a surface of the substrate 10 away from the outer shell 50, to expose the external pad 13. The external pad 13 is for realizing the electrical connection of the whole optical sensor package structure 100. Generally, the external pad 13 is electrically connected to an external circuit board by connecting wires.

In another embodiment of the present disclosure, the optical sensor package structure 100 includes a plurality of the signal processing chips 20. The plurality of the signal processing chips 20 are provided on the surface of the substrate 10 at intervals, and each signal processing chip 20 is provided with a conductive through hole 21. Each signal processing chip 20 is electrically connected to the substrate 10 via the conductive through hole 21, and the optical sensor package structure 100 includes a plurality of the photodiodes 30 corresponding to the signal processing chips 20. One of the photodiodes 30 is provided on the surface of the signal processing chip 20 away from the substrate 10 and is electrically connected to the substrate 10 by a corresponding conductive through hole 21. The potting adhesive layer 60 is for wrapping each signal processing chip 20 and a corresponding photodiode 30.

Correspondingly, the outer shell 50 is provided with a plurality of first installation through grooves 51, and a corresponding signal processing chip 20 and a corresponding photodiode 30 are provided in a first installation through groove 51. The potting adhesive filled in each first installation through groove 51 is for wrapping a corresponding signal processing chip 20 and a corresponding photodiode 30. The optical sensor package structure 100 includes a plurality of the signal processing chips 20 and a plurality of corresponding photodiodes 30, to realize multiple functions. In an embodiment, the signal processing chip 20 may be an analog front-end chip, an accelerometer chip, a power management chip, an electrocardiogram chip, etc.

The present disclosure further provides an electronic device, and the electronic device includes the optical sensor package structure 100 as mentioned above. The specific structure of the optical sensor package structure 100 can be referred to the foregoing embodiments. Since the electronic device adopts all the technical solutions of all the foregoing embodiments, it at least has all the beneficial effects brought about by the technical solutions of the foregoing embodiments, which will not be repeated here.

It should be noted that the electronic device includes an outer shell 50, and a circuit board is provided inside the outer shell 50. The optical sensor package structure 100 is installed and fixed in the outer shell 50, and the method for installing and fixing the optical sensor package structure 100 in the outer shell 50 can be a method by buckle fixing, screw fixing, adhesive fixing or other reasonable and effective method. The outer shell 50 is provided with a detection port corresponding to the light emitting diode 40 of the optical sensor package structure 100, to enable the light emitted by the light emitting diode 40 to pass through the detection port. The external pad 13 of the substrate 10 in the optical sensor package structure 100 is electrically connected to the circuit board inside the outer shell 50 by connecting wires, to realize the function of the optical sensor. The electronic device is generally a wearable electronic device, such as a mobile phone, a watch, an earphone, a bracelet, etc.

The above are only some preferred embodiments of the present disclosure, and do not limit the scope of the present disclosure thereto. Under the concept of this disclosure, any equivalent mechanism transformation made according to the description and drawings of the present disclosure, or direct/indirect application in other related technical fields are included in the scope of the present disclosure.

What is claimed is:

1. An optical sensor package structure, comprising:
a substrate;
a signal processing chip provided on a surface of the substrate, wherein the signal processing chip is provided with a conductive through hole, and the signal processing chip is electrically connected to the substrate via the conductive through hole;
a photodiode provided on a surface of the signal processing chip away from the substrate, wherein the photodiode is electrically connected to the substrate via the conductive through hole; and
a potting adhesive layer, wherein the potting adhesive layer is for wrapping the signal processing chip and the photodiode, and an elongation at break of the potting adhesive layer is greater than 40%,
wherein:
a surface of the substrate facing the signal processing chip is provided with a first pad,
a surface of the signal processing chip facing the substrate is provided with a redistribution layer,
the signal processing chip is electrically connected to the first pad via the conductive through hole and the redistribution layer,
the surface of the signal processing chip facing the substrate is provided with a solder ball, and the solder ball is electrically connected to the redistribution layer, and
the first pad is provided with a solder joint, and the solder ball is electrically abutted against the solder joint.

2. The optical sensor package structure of claim 1, wherein a Young's modulus of the potting adhesive layer is lower than 100 MPa.

3. The optical sensor package structure of claim 1, wherein a distance between a surface of the potting adhesive layer away from the photodiode and a surface of the photodiode away from the signal processing chip is L, and L is greater than 0 mm and not greater than 0.1 mm.

4. The optical sensor package structure of claim 1, wherein a photoelectric electrode of the photodiode is configured to face the signal processing chip, and the photoelectric electrode is electrically connected to the substrate via the conductive through hole.

5. The optical sensor package structure of claim 4, wherein the photodiode comprises two photoelectric electrodes provided on a same side of the photodiode, and when the two photoelectric electrodes are installed, the two photoelectric electrodes are configured to face the signal processing chip and electrically connected to the substrate.

6. The optical sensor package structure of claim 1, further comprising an outer shell, wherein:
the outer shell is provided on the surface of the substrate facing the signal processing chip, and a surface of the outer shell away from the substrate is provided with a first installation through groove for exposing the substrate; and the signal processing chip and the photodiode are provided in the first installation through groove, and the potting adhesive layer provided in the first installation through groove is for wrapping the signal processing chip and the photodiode.

7. The optical sensor package structure of claim 6, further comprising a light emitting diode, wherein:
the light emitting diode is provided on the surface of the substrate facing the signal processing chip and is electrically connected to the substrate;
the surface of the outer shell away from the substrate is further provided with a second installation through groove for exposing the substrate; and
the light emitting diode is provided in the second installation through groove, and the potting adhesive layer is further provided in the second installation through groove and is for wrapping the light emitting diode.

8. The optical sensor package structure of claim 7, wherein a transmittance of the potting adhesive layer to a light emitted by the light emitting diode is greater than 90%.

9. The optical sensor package structure of claim 7, wherein:
the second installation through groove comprises an installation groove section and a light guide groove section, the installation groove section and the light guide groove section are sequentially distributed along a direction away from the light emitting diode, and the installation groove section and the light guide groove section are connected with each other, and
the light emitting diode is provided in the installation groove section, and an area enclosed by the light guide groove section gradually increases along the direction away from the light emitting diode.

10. The optical sensor package structure of claim 7, wherein:
the surface of the substrate facing the signal processing chip is provided with a second pad and a third pad; and
the light emitting diode is provided with two light emitting electrodes, one of the two light emitting electrodes is electrically connected to the second pad, and the other of the two light emitting electrodes is electrically connected to the third pad.

11. The optical sensor package structure of claim 10, wherein the light emitting electrode comprises a light emitting negative electrode and a light emitting positive electrode, the light emitting negative electrode is electrically connected to the second pad, and the light emitting positive electrode is electrically connected to the third pad.

12. The optical sensor package structure of claim 1, wherein:
the optical sensor package structure comprises a plurality of the signal processing chips, the plurality of the signal processing chips are provided on the surface of the substrate at intervals, each signal processing chip is provided with a conductive through hole, and each signal processing chip is electrically connected to the substrate via the conductive through hole;
the optical sensor package structure comprises a plurality of the photodiodes corresponding to the signal processing chips, and one of the photodiodes provided on the surface of the signal processing chip away from the substrate is electrically connected to the substrate via a corresponding conductive through hole; and
the potting adhesive layer is for wrapping each signal processing chip and a corresponding photodiode.

13. An electronic device, comprising the optical sensor package structure of claim 1.

\* \* \* \* \*